(12) United States Patent
Müller-Chorus et al.

(10) Patent No.: US 7,036,917 B2
(45) Date of Patent: May 2, 2006

(54) DEVICE FOR PARALLEL METERING OF LIQUIDS

(75) Inventors: Birgit Müller-Chorus, Münster (DE); Ralf-Peter Peters, Borgisch-Gladbach (DE); Holger Bartos, Dortmund (DE)

(73) Assignee: Steag Microparts GmbH, Dortmund (DE)

(*) Notice: Subject to any disclaimer, the term of this patent is extended or adjusted under 35 U.S.C. 154(b) by 178 days.

(21) Appl. No.: 10/728,111

(22) Filed: Dec. 5, 2003

(65) Prior Publication Data
US 2004/0183869 A1    Sep. 23, 2004

(30) Foreign Application Priority Data
Dec. 6, 2002    (DE) ................................. 102 57 004

(51) Int. Cl.
*B41J 2/17*    (2006.01)
(52) U.S. Cl. ......................................................... 347/84
(58) Field of Classification Search .................... 347/2, 347/7, 54, 68, 85, 84; 141/2, 18; 277/318
See application file for complete search history.

(56) References Cited
U.S. PATENT DOCUMENTS
3,631,724 A * 1/1972 Oster et al. ............... 73/864.13
3,946,398 A * 3/1976 Kyser et al. ................... 347/70
4,019,721 A * 4/1977 Langner .................... 366/160.3
4,380,018 A * 4/1983 Andoh et al. .................. 347/68
6,629,739 B1 * 10/2003 Korol ........................... 347/10

* cited by examiner

*Primary Examiner*—Anh T. N. Vo
(74) *Attorney, Agent, or Firm*—Hoffman, Wasson & Gitler P.C.

(57) ABSTRACT

A device for parallel metering of a liquid with the following features:
  the device has a first body;
  the first body has a main channel, secondary channels, one inlet and outlets;
  the main channel is connected to the inlet;
  the secondary channels are connected to one outlet at a time;
  the secondary channels are connected to the main channel;
  the device has at least one first chamber with a first pressure medium;
  the first body has means for transferring transfer means pressure surges of the pressure medium from a first chamber to the secondary channels;
  each transfer means is connected to a secondary channel; and
  at least one means for preventing a fluidic connection between the secondary channels and the chamber is assigned to the transfer means.

44 Claims, 3 Drawing Sheets

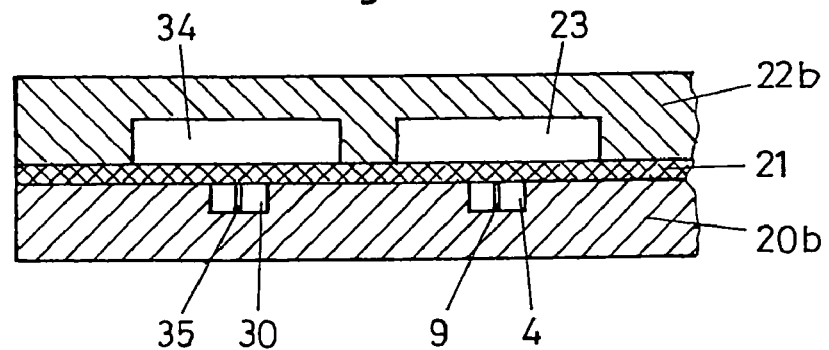
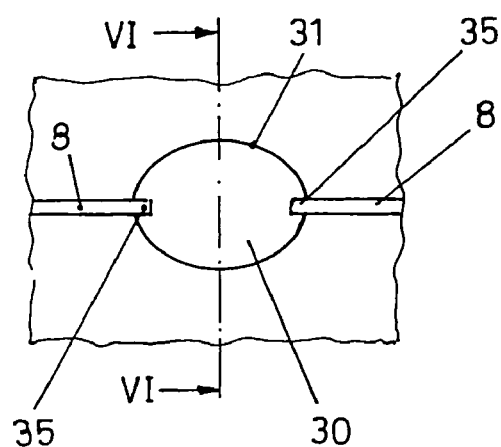
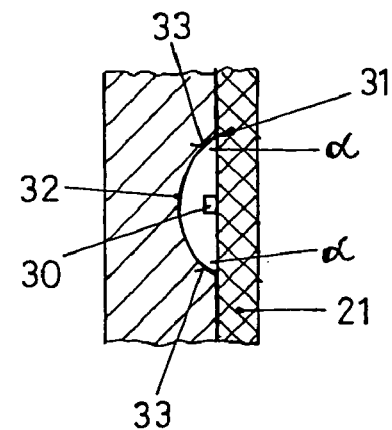
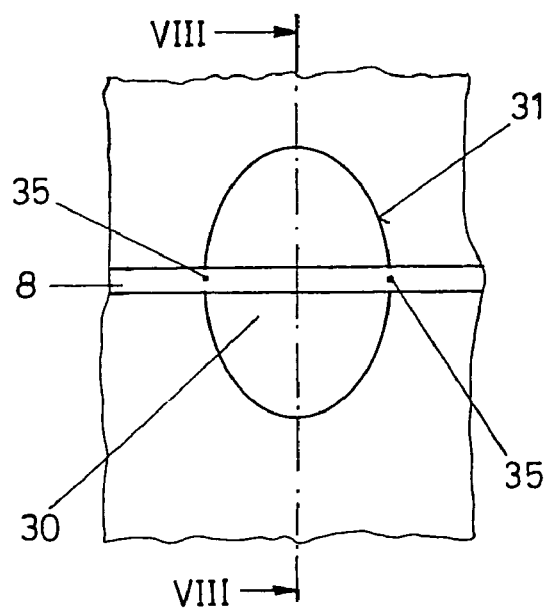
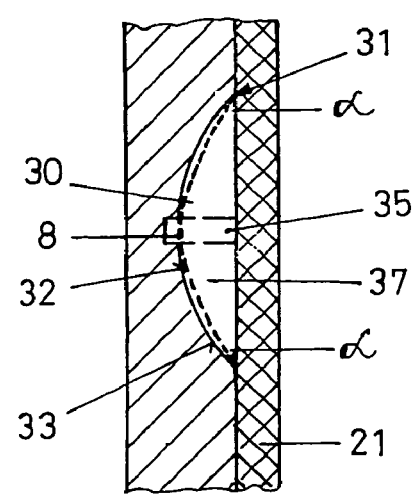

DEVICE FOR PARALLEL METERING OF LIQUIDS

BACKGROUND OF THE INVENTION

This invention relates to a device for the parallel metering of a liquid. For this purpose, the device has a first body in which there are a main channel, secondary channels, one inlet, and outlets. The main channel is connected to the inlet, while the secondary channels are connected to one outlet at a time. Furthermore, the secondary channels are connected to the main channel. The first body for delivering the metered liquid has means for transferring pressure surges of a first pressure medium from a first chamber to the secondary channels. Each of these transfer means is connected to a secondary channel.

Such a device is known from document WO 99/42805. The device disclosed in this document for the parallel metering of a liquid of the initially mentioned type as the transfer means for transfer of the pressure surges which are imparted to the metered amounts of liquid for emptying the device has small channels which adjoin the secondary channels. All these channels which are made as transfer means discharge into a pressure surge collecting channel. This collecting channel is subjected to pressure surges from a device for producing pressure surges, which is located outside of the device for parallel metering of a liquid. The pressure surges are accommodated by the collecting channel and are routed via the channels which are made as transfer means to the secondary channels and thus to the metered liquids. In doing so, among others, due to the different distances of the transfer means to a pressure medium connection of the collecting channel, time differences in the action of the pressure surges on the metered liquids can occur. This can result in the first secondary channel or the first secondary channel arrangement consisting of an outlet and a secondary channel being emptied while other channels still contain the metered liquid. Sometimes this can be quite desirable, but if the first secondary channel or the first secondary channel arrangement is already emptied, the collecting channel is vented via the channel which is made as the transfer means and the secondary channel toward the inlet. The metered liquids contained in it are not expelled. An effective use of this device is only possible with special consideration and determination of the distribution of the pressure surge in the collecting channel.

The document with publication number U.S. Pat. No. 6,196,664 B1 discloses a device for delivering ink jets for printers in which inkjets can be delivered from outlets. These outlets are supplied with ink via secondary channels which are connected to the main channel. The delivery of ink is caused by several pressure generation means in the form of piezoelectric elements, such a piezoelectric element being assigned to each outlet. The assignment of a piezoelectric element to each outlet is necessary since the outlets must be triggerable separately from one another to produce different print formats.

The device described in the documents becomes technically complex due to the assignment of one piezoelectric element to each of the outlets.

Furthermore, the document with publication number US 2001/0038402 discloses a device in which there are outlets, which are located in a two-dimensional grid and through which droplets can be discharged from the device. The outlets that are arranged in a grid shape are connected via secondary channels to the main channel. A pressure surge on one side wall of the main channel can be transferred to the wall of the main channel for example by mechanical pressure and from there to the secondary channels which expel droplets of the liquid which fills the main channel and the secondary channels via the outlets. For this purpose these outlets have piezoelectric elements, which can open or close the outlets so that each of the outlets via which droplets are delivered can be determined individually. This is necessary for example for a use of the device as claimed in the invention as the printing head for inkjet printers in order to be able to produce different print formats.

The pressure which is applied to eject liquid onto the side wall of the main channel acts in the lengthwise direction of the secondary channels and perpendicular to the direction of primary extension of the main channel. The side wall is supported at least on one end. At the same time, the pressure which is applied to the side wall is uniform over the length of the side wall. Part of the force which acts on the side wall is accommodated here by the support of the side wall, another part leads to deflection of the side wall. In this way the side wall is deflected differently in individual sections; this causes a locally different pressure wave in the main channel. The pressure distribution within the main channel and accordingly also the secondary channels is therefore different, which leads to different amounts being expelled via the outlets. Metering with relative accuracy as is known for example from document WO 99/42805 is not possible with the device according to document US 2001/0038402 A1.

Finally, the prior art discloses a document with publication number WO 02/060582 A2. This publication discloses microfluidic devices for dispensing liquids from a microfluidic system. The document discloses a host of so-called peristaltic pumps by which a liquid can be advanced in a channel. In doing so, at successive locations in a time sequence a pressure surge is applied to the wall of the channels, which is moving the liquid in the channel in the two lengthwise directions of the channel. The liquid can thus be advanced in a preferred lengthwise direction by the pressure surges, which are matched in time. In FIGS. 8a and 8b a device is disclosed in which there are several channels next to one another which are exposed in parallel to pressure surges in order to advance a liquid at the same time in the channels. Metering with this device is not possible.

Therefore it is an object of the invention is to provide a device for parallel metering of a liquid of the initially mentioned type in which all secondary channel arrangements can be uniformly emptied even if a pressure surge is acting in time with different delays on the secondary channels or the secondary channel arrangements.

Another object is to provide a device, which is made technically less complex and with which parallel metering of small amounts of liquid with relative accuracy is possible.

An object of the invention is furthermore to provide a device which is simple to handle, suitable for operation by automatic devices, economical to produce, and which is suited to the materials used and as a disposable article.

SUMMARY OF THE INVENTION

In such a device, the transfer means and thus the secondary channel arrangements are assigned at least one means for preventing the fluidic connection of the secondary channels to the chamber. This means for preventing a fluidic connection thus prevents venting of the device via the means for transferring the pressure surges after the assigned secondary channel has been emptied via the respective outlet. This ensures that the secondary channel arrangements can also be emptied in succession in time and the metered liquids contained in them can be expelled. The pressure surge that causes emptying can be produced by a single means for producing a pressure surge which expels the metered liquid from the device.

In the main channel, the device can have controllable means for flow decoupling (decoupling means). These decoupling means can be located between the inlet and the first connection of the main channel to one of the secondary channels. Alternatively or in addition, between all connections of the main channel and one of the secondary channels there can be decoupling means in the main channel. The secondary channel arrangement can be fluidically decoupled from the inlet by a decoupling means in the main channel between the inlet and the first connection of the main channel to one of the secondary channels. The decoupling causes the pressure waves not to be routed out of the secondary channel arrangements via the main channel to the inlet. In any case it is conceivable for the pressure wave to be relayed very highly damped to the inlet. So that a pressure wave from the system of secondary channels is transferred only very damped or not at all to the main channel, it is for example sufficient to clearly increase the flow resistance in the main channel by the decoupling means.

If conversely there are also decoupling means between the individual secondary channels, pressure waves that run in one secondary channel are not relayed to the others, especially the adjacent secondary channels, since this is prevented by the decoupling means.

A decoupling means between the inlet and the first connection of the main channel to one of the secondary channels and/or between all connections of the main channel to one of the secondary channels enables more accurate metering of the liquids which are to be delivered from the metering device. This becomes apparent especially against the background of the document with publication number U.S. Pat. No. 6,196,664 B1. In the embodiment disclosed in this document, metering, especially accurate metering by means of the disclosed device, is not possible.

This is due to the following particular of the device, which is described in the document. The piezoelectric element and the assigned outlet are on opposing sides of the secondary channel in the side walls of the secondary channel. A pressure surge which sprays ink out of the assigned outlet and which is produced by the piezoelectric element causes a pressure wave in the secondary channel which runs on the one hand perpendicular to the direction of primary extension of the secondary channel for spraying out the ink, and on the other runs in the lengthwise direction of the secondary channel. The ink from the secondary channel can be conveyed back into the main channel by the pressure wave, which is propagating in the lengthwise direction of the secondary channel and by the connection of the secondary channel via the main channel to other secondary channels, and from the main channel under certain circumstances can travel into other secondary channels. This can lead to displacement of parts of the ink into other secondary channels, which makes impossible accurate metering of the ink which is sprayed out via the outlets. The device disclosed in the document is used for parallel delivery of ink; metering of a consumed amount with sufficient accuracy is however not possible with the device.

The decoupling means can be valves.

According to the invention, the prevention means can be a first elastic and at least essentially impermeable film. This film prevents a fluidic connection between the secondary channels via the transfer means to the other device. As claimed in the invention the film can be a plastic film, an elastomer film or a silicon film.

The main channel and secondary channels as claimed in the invention can be grooves that are provided in the first outer surface of the first body. The main channel and/or the secondary channels as claimed in the invention can be capillaries at least in sections. This enables or prevents in certain sections of the main channel or secondary channels the transport of a liquid without external forces. It is especially advantageous if the sections of the secondary channels adjoining the main channel are capillaries. Transport into the capillaries is enabled for example if the acting capillary forces after wetting the channel boundary surfaces drive the liquid in the channel forward. To do this the channel must be vented. If venting is not possible, transport in capillaries is not possible. If therefore in the device as claimed in the invention there are especially sections of the secondary channels which are not vented, transport of the liquid in this section of the secondary channel is not possible.

The transfer means are made advantageously as first recesses, and these first recesses can then be located on the first end of each secondary channel, while the outlets are located on the second ends of each secondary channel. The first recesses at least in one area in which the secondary channels enter the first recesses have a lateral boundary surface, which is as perpendicular as possible to the outside surface of the first body in which the first recess is made.

The first film can lie on the first outside surface of the first body. The first film can be attached to the first body by bonding. The first film can cover at least the first recesses and thus can prevent a fluidic connection out of the secondary channels via the first recesses to the remaining device. The first film as claimed in the invention can be attached to the body in the area of the first recess by bonding so that the film in the areas that adjoin the edge of the recess is securely connected to the first body.

The device can have a second body. The second body can rest on the first film, the second body and the first film advantageously encompassing at least the first chamber. The first chamber can be fluidically connected to the means for producing pressure surges. This chamber can fundamentally be of any shape and there can also be elements, which project into the chamber. The individual areas of the chamber should however be connected to one another.

The first chamber with the interposition of the first film can be connected to the transfer means for transferring the pressure surges. The second body can have microstructure elements that project advantageously into the chamber. These microstructure elements can for example be used to fix the first film to the first body. The first film would then be clamped between the microstructure elements and the first body. It is thus possible for example to fix the first film in the area of the first recesses on the first body.

Because the first recesses in the area of the entries of the secondary channels into the first recesses are vertical, the first film is prevented from arching into the first recess when a pressure is applied such that the entries of the secondary channels into the first recess are closed. The pressure surges can therefore be transferred into the secondary channels.

The first pressure medium with which the first chamber is filled can be under a pressure which has a first amount and which ensures that the first film is fixed on the first body. If the pressure of the pressure medium is increased to a second amount, for example the valves that form the decoupling means can be closed. To do this the first chamber would also have to overlap the valves. If the pressure is increased to a third amount by a pressure surge, this pressure surge is delivered via the first film to the first transfer means which then causes the liquids to be expelled from the device.

The first chamber of a device can have a height from 0.1 mm to 3 mm.

According to the invention, the device can itself also have a means for producing pressure surges. The pressure surges can also be delivered to the film directly by a mechanical or electromechanical means. The means for producing pressure surges are for example piezoelectric elements, electromagnets or other electromechanical or mechanical means.

The first chamber can preferably have a wall which is formed by the second body and which can be deflected under the action of a means for producing a pressure surge into the interior of the chamber, by which the pressure surge in the chamber is produced.

In the secondary channels there can be means for metering (metering means) the liquid. The metering means are provided advantageously between the outlets and the connection between the assigned secondary channel and the main channel. The device can have as metering means second recesses in the first or in another outside surface of the body. These second recesses can be covered by the membrane, by a second film or a cover.

The valves of the device can be formed by a third recess and a film, i.e. either the first or the second or the third film. It is furthermore conceivable that there are also valves in the secondary channels.

The first chamber can overlap the first, second or third film in the area of the third recess or the third recesses. The second body and the first body can however also encompass a second chamber which overlaps the first, second or third film in the area of the third recess. The second chamber can contain a second pressure medium which acts on the sections of the first, second or third film which are assigned to the third recesses.

The first and the second chamber can be separately triggerable.

The third recesses can have lateral boundary surfaces which fall away flatly from at least one part of the edges to the bottom. The recess can thus simulate the shape of the films arching into the third recess under the action of a pressure surge. Thus it is possible for the film to distinctly increase the flow resistance of the valve or to make a connection via the valves impossible. The flatly sloping lateral boundary surfaces can be tilted at an angle between 5 to 45 degrees.

The third recesses can have a concave arch which can be for example spherical, but also aspherical. The arch can moreover also be cylindrical.

The device between the two inlet openings of the sections of the main channel into at least part of the third recesses can have a bridge which extends from the first edge via the lateral boundary surfaces and the bottom to the second edge. This bridge projects in the direction of the film which covers the third recess so that when the film is deflected when pressure is applied accordingly, the film comes to rest on the bridge and thus fluidically separates the two entry openings of the sections of the main channel from one another.

The third recesses of the device as claimed in the invention can have a depth which corresponds to 0.9 to 1.5 times the depth of the main channel. If the third recess has a depth which corresponds to 0.9 to 1 times the depth of the main channel, the two inlet openings of the main channel sections can be connected via a groove in the bottom or in the side boundary surfaces of the recess.

The liquid which is to be metered can rise either into the main channel and the secondary channels for filling the device via capillary action, or a pressure gradient forces or intakes the liquid into the main channel and the secondary channels.

The volumes of the metering means and/or of the secondary channels and/or of the main channel can fix the volume of the amount of liquid which can be metered, by which a liquid excess can be minimized. The outlets for the liquid can be matched to a suitable grid size (for example 4.5 or 2.25 mm) so that the liquids can be dispensed precisely for example into a microliter plate.

In the device, there can be both a central means for producing pressure surges, but there can also be individually controllable means for producing pressure surges for each secondary channel. The outlets can be opened when the liquid is added to the main channel and the secondary channels so that the air contained in the channels can escape. After filling, these outlets are then closed. For this purpose there can be means for closing the outlets. The means can be for example an elastic mat.

In the device, reagents can already have been added. They can be added especially in the area of the transfer means, at the outlets and the secondary channels, in the valves or in the metering means. Thus it is possible to carry out reactions for example for analyses within the device. The reagents can be for example chemicals, oligonucleotides, so-called magnetic balls, dyes, peptides, proteins, fats or others. The reactions can be carried out in the device itself or also after leaving the device, for example, in a microliter plate.

In other embodiments of the device, other process steps can be enabled. They can be for example the washing of bound or absorbed substances or of so-called magnetic beads. The reactions which have been carried out on the device can be evaluated in or after (partial) emptying via the outlets outside the device.

Furthermore there can be means for temperature treatment which temperature-treat at least parts of the device before, during or after the reactions.

The amount of liquid which is to be dispensed per secondary channel arrangement as claimed in the invention can be in the range of picoliters to milliliters, but preferably liquid amounts in the range of nanoliters to microliters are preferred.

Furthermore it is conceivable for individual recesses, capillary stops and/or valves to be triggered individually and purposefully. This can be achieved for example by the recesses being made geometrically (aspect ratio) such that at different threshold values in a preestablished sequence it is closed or actuated by the pressure on one of the membranes.

The first body can be made from plastics (for example by molding, stamping, cutting or casting), metal, wax, rubber, silicon, glass, ceramic or the like. It is likewise conceivable for the system consisting of channels and recesses to be located on the two sides of the first body. In this way the number of amounts of liquid which can be metered on a small space can be increased.

BRIEF DESCRIPTION OF THE DRAWINGS

Embodiments of the device as claimed in the invention are detailed using the drawings.

FIG. 4 shows a section through the first body according to FIG. 2 along the kinking line IV—IV, the individual elements in part being shown only schematically;

FIG. 5 shows an overhead view of a valve in an actual version;

FIG. 6 shows a section through the valve according to FIG. 5 along the line VI—VI;

FIG. 7 shows an overhead view of a second valve in an actual version;

FIG. 8 shows a section through the valve according to FIG. 7 along the line VIII—VIII;

DETAILED DESCRIPTION OF THE INVENTION

Figure 1:
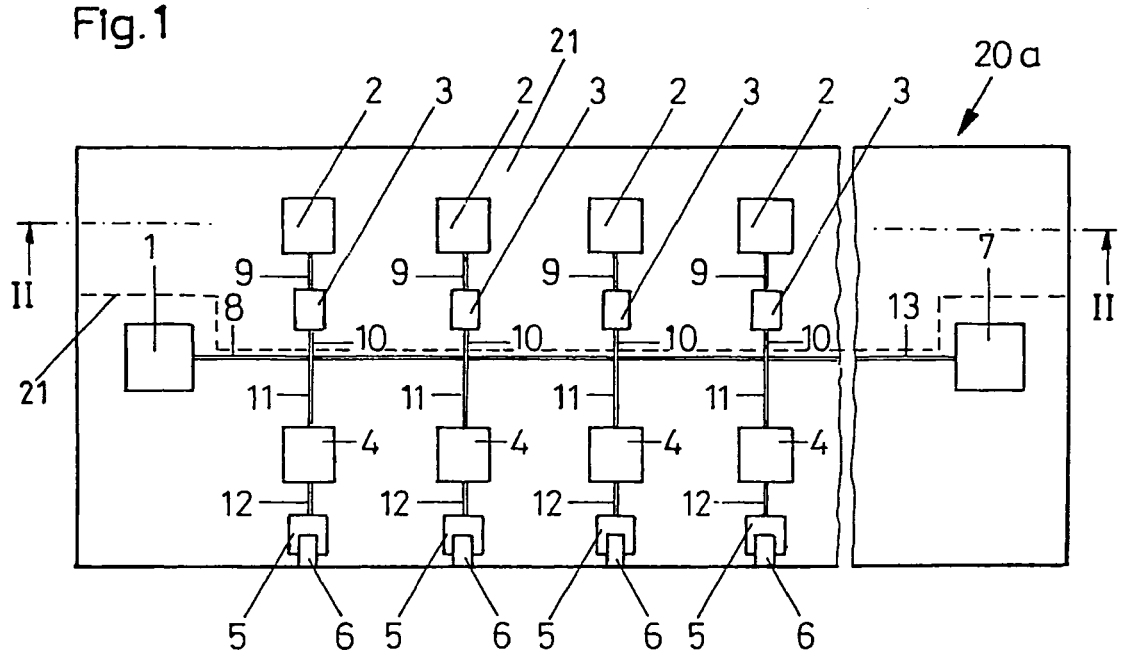
FIG. 1 shows a first body of a first embodiment in an overhead view, the individual elements in part being shown only schematically.
Figure 2:
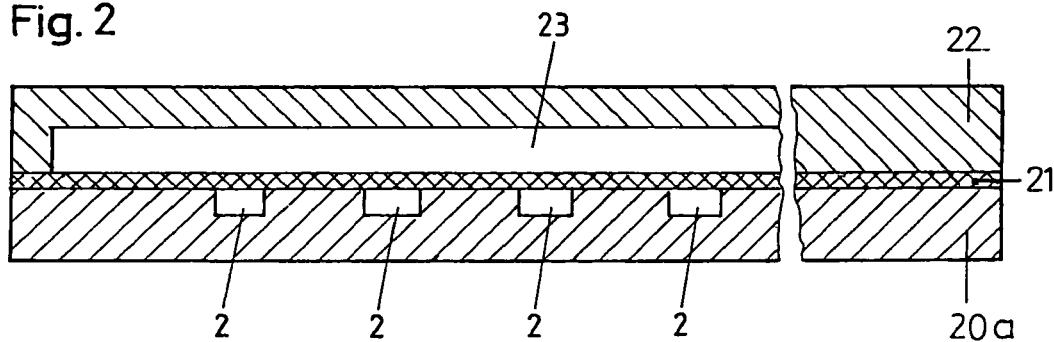
FIG. 2 shows a section through the first body according to FIG. 1 along line II—II, the individual elements in part being shown only schematically.

The first body 20 of a device for parallel metering of a liquid and if necessary for parallel dispensing of a liquid—for example onto a microliter plate—which is shown in FIGS. 1 and 2 has one inlet 1 for the liquid which is to be metered and a number of outlets 6. The inlet 1 and the outlets 6 are connected to one another by a system of channels. The system of channels consists of a main channel 8 and secondary channels 9, 10, 11, 12, one outlet 6 being assigned to each secondary channel 9, 10, 11, 12 (secondary channel arrangements). The system of channels furthermore includes a channel 13 which is routed to a waste collector 7.

The secondary channels 9, 10, 11, 12 are divided into several channel sections 9, 10, 11, 12. The two channel sections 10, 11 branch off directly from the main channel 8 in opposite directions at a right angle from the main channel 8.

The channel section 10 of each secondary channel 9, 10, 11, 12 discharges into a first (schematically shown) capillary stop 3 from which each secondary channel 9, 10, 11, 12 continues with the secondary channel section 9 as far as to a first recess 2.

The channel section 11 of each secondary channel 9, 10, 11, 12 discharges into a second (schematically shown) recess 4. The channel section 12 of each secondary channel 9, 10, 11, 12 leads from this second recess 4 to a capillary stop 5. These second capillary stops 5 adjoin one outlet 6 at a time.

The waste collector 7 is formed by another (schematically shown) recess 7 which is vented via a channel which is not shown.

Both the first recess 2, the second recess 4, the other recess 7, the main channel 8 and also the secondary channel sections 9, 10, 11, 12 are made in one surface of the first body 20a. This means that the recesses 2, 4, 7 of the main channel 8 and the secondary channel sections 9, 10, 11, 12 are open to the top. The secondary channel sections 9, 10, 11, 12 and the main channel 8 are provided as grooves in the surface of the first body 20a. Basically it is also conceivable to provide the recesses and channels on different surfaces of the first body 20a.

The first capillary stop 3 and the second capillary stop 5 are likewise made in the form of recesses in the surface of the first body 20a.

The surface of the first body 20a to which the recesses 2, the secondary channel sections 9, 10, 11, the main channel 8 and the first capillary stop 3 are opened, is, as indicated by the broken line in FIG. 2, is covered by a film 21. This film 21 is adjoined by a second body 22, as likewise indicated in FIG. 2 by the broken line. The other cavities 4, 5, 7, 12 in the surface of the body are conversely covered directly by the second body 22. Here, above the first recesses 2 and the first capillary stop 3 between the film 21 and the second body 22 a chamber 23 is formed. This chamber 23 is advantageously formed, as shown in FIG. 2, by a correspondingly large recess in the second body 22.

The covering of the first recesses 2 of the main channel 8, of the first capillary stop 3 and of the secondary channel sections 9, 10, 11 by the film 21 results in that the aforementioned first recesses 2, the main channel 8, the secondary channel sections 9, 10, 11 and the capillary stops 3 are bounded to the top, i.e. toward the outside of the first body 20a. The other cavities are conversely bordered by the second body 22. This results in that a liquid which has travelled via the inlet 1 into the system of channels or recesses and capillary stops which are located in the channels or on their end can be removed again only via the outlets 6 or the waste collector 7 from the arrangement of the first body 20a and the film 21, or the first body 20a, the film 21 and the second body 22.

The recesses 2 are made such that the film 21 when exposed to the corresponding pressure can penetrate from the outside into the cavities which are formed by the recesses 2.

The capillary stops can be formed for example by simple widenings of the channels. But they can alternatively also have a water-repellant coating which prevents the passage of liquid through the capillary stop.

The penetration depth of the film 21 into the indicated cavities can be adjusted by the shape and size of the cavities among others by the so-called aspect ratio. In doing so the aspect ratio designates simply the ratio of the depth of the recess to its width. The channels, i.e. the main channel 8 and the secondary channel sections 9, 10, 11, 12, can also be identified by an aspect ratio, the aspect ratio in the channels being set such that when the film 21 is exposed to pressure from the outside the film 21 does not close the channels.

The second recesses 4 are provided in the first body 20a as means for metering of the liquid which has been introduced into the first body 20a via the inlet 1. This means that the recesses 4 have a volume which corresponds essentially to the volume which is to be delivered via the outlets 6 and which is to be metered. Here it must be considered that in the channel sections 10, 11, 12 liquid can be contained which is dispensed with high probability likewise via the respective outlet 6. In doing so, for the first body 20a the capillary stop 3 between the channel sections 9 and 10 in each secondary channel prevents entry of the liquid into the channel section 9 and moreover into the first recess 2.

The first recess 2 is set up as a means for transfer of a pressure surge. From the outside via this transfer means a pressure surge is routed into each of the secondary channels 9, 10, 11, 12 which then presses entirely or partially the liquid contained in the secondary channel sections 10, 11, 12 and in the means for metering, i.e. in the second recesses 4, via the respective outlets 6 out of the device for metering.

To produce a pressure surge in the secondary channel arrangements either by the means for pressure generation provided in the metering device or by an external pressure generation means, a pressure surge is routed into the chamber 23 which is provided between the film 21 and the second body 22. The pressure surge propagates via the film 21 to the first recesses 2. From these first recesses 2 which therefore are called means for transfer (transfer means) of a pressure pulse the pressure surge propagates then via the secondary channels to the outlets 6 and in doing so forces the amounts of liquid in the secondary channel sections 10, 11, 12 and the metering means out of the first body 20a.

When the metered amount of liquid contained in the first body 20a is thrown out of one of the secondary channel arrangements of secondary channel sections 10, 11, 12 and the metering means (second recess 4), the film 21 prevents venting of the pressure which has built up furthermore in the recess between the membrane 21 and the second body 22 via these secondary channel arrangements. This would lead under certain circumstances to there no longer being sufficient pressure in the recess between the film 21 and the second body 22 in order to empty the other secondary channel arrangements of the device, i.e. to throw the metered liquid out of these secondary channel arrangements.

Before the liquid which has been introduced into the device as claimed in the invention is expelled in metered form via the outlets 6, the liquid contained in the main channel 8 can be drained. To do this, either an overpressure is applied at the inlet 1 and forces the amount of liquid contained in the main channel 8 via the channel 13 toward the waste collector 7 or a negative pressure which sucks the liquid out of the main channel 8 via the channel 13 is applied at the waste collector 7. Transport can also take place by the action of capillary forces.

Figure 3:
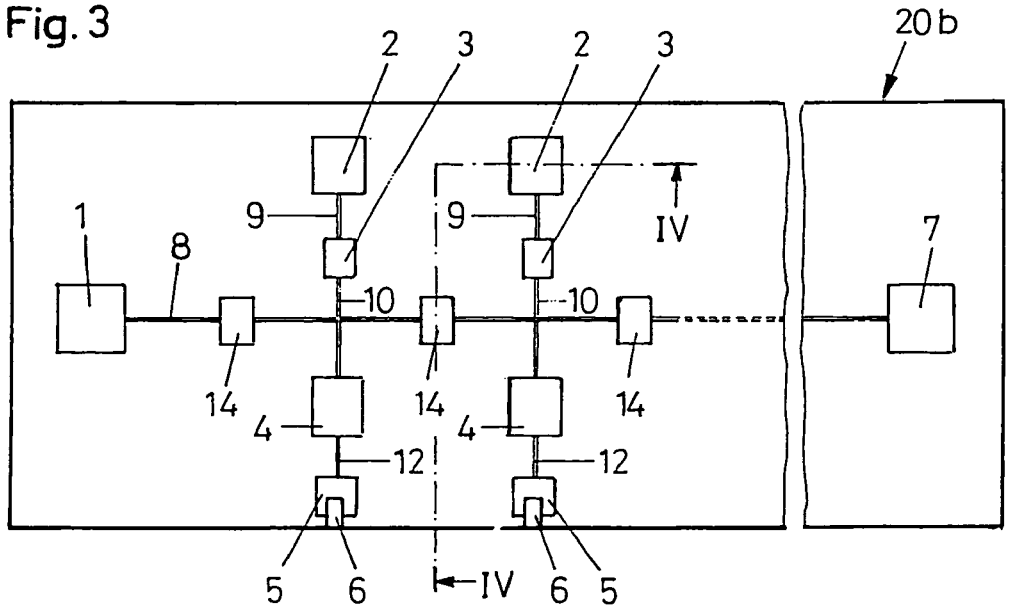
FIG. 3 shows a first body of a second embodiment in an overhead view, the individual elements in part being shown only schematically.

This emptying of the main channel 8 is advantageous if for example in a device with a first body 20b according to FIGS. 3 and 4 there are valves 14 in the main channel 8. These valves 14 which are shown schematically in FIGS. 3 and 4 are each provided between the main channel 8 and the secondary channels upstream and downstream of a connecting point. In this way the individual secondary channel arrangements can be decoupled from one another. The valves 14 therefore form decoupling means. As soon as the valves 14 are blocked, a connection between the two secondary channel arrangements via the main channel 8 is no longer possible. The valves 14 are advantageously provided as a combination of a third recess and the first film 21. The second body has a recess which overlaps the valves 14 and thus forms a second chamber 34. For the valves 14 and the third recesses and the sections of the first film which cover these third recesses the aspect ratio dictates whether and at what pressure the film 21 prevents penetration of liquid through the third recess of the valve 14. Likewise, in this way separate triggering of the outlets is possible.

The emptying of the main channel 8 for these valves 14 is a good idea before actuating the valves 14, since otherwise the space in the recess is occupied by an incompressible liquid which makes it difficult to close the recess by the film 21 when the film 21 is exposed to the corresponding pressure, or when the valves 14 are actuated, the liquid is forced into the inlet 1, the waste collector 7 or the first recesses 2.

Decoupling the secondary channel arrangements via the valves 14 makes it possible, with a corresponding set-up or exposure of the means for transferring the pressure pulse, to trigger the secondary channel arrangements separately from one another. After the first secondary channel arrangement has been emptied, the film 21 as a prevention means also prevents a fluidic connection from the secondary channel section 9 and the first recess 2 to the part of the metering device which lies on the other side of the film 21. In this way the chamber which is formed between the film 21 and the second body 22 cannot be vented via the secondary channel arrangement which has been emptied first.

The embodiment which is enlarged in FIGS. 5 and 6 for a valve has a third recess 30 which has a concave arch which has the shape of a section of an ellipsoid of rotation. Proceeding from the valve there extend sections of the main channel 8 which discharge via inlet openings 35 into the third recess 30. The recess 30 and the adjoining sections of the main channel 8 are covered by a first film 21. From the edge 31 of the recess 30 the lateral boundary surfaces 33 fall away flat toward the bottom 32 of the recess. The angle between the side boundary surfaces 33 and the outside surface of the first body which adjoins the first film 21 in the area of the valve is smaller than 45°.

To actuate the valve which is shown in FIGS. 5 and 6, the pressure medium which is contained in the second chamber 34 which overlaps the third recess 30 is exposed to a pressure, the film 21 is pressed to the inside in the area of the recess 30. In this way the flow resistance between the entry openings 35 of the sections of the main channel 8 is increased. If the pressure on the first films 21 in the area of the third recess 30 is large enough, the first film 21 comes to rest flat even on the bottom 32 and the side walls 33, where a fluidic connection between the entry openings 35 is impossible.

One version of the first valve which is shown in FIGS. 5 and 6 is the second valve which is shown in FIGS. 7 and 8. The two valves differ in that the depth of the third recess 30 is less in the second valve according to FIG. 7 or 8 relative to the depth of the main channel. In this way the main channel 8 in the form of a groove is pulled through the third recess 30. The groove in the bottom 32 through the third recess 30 when the valve is opened has the advantage that when a liquid enters which is to be routed through the main channel 8 and through the valve, at least the groove in the bottom 32 of the valve can be wetted without the action of external forces. The meniscus of a liquid can therefore be moved solely as a result of capillary forces by the valve from one entry opening 35 to the opposing entry opening 35.

Figure 9:
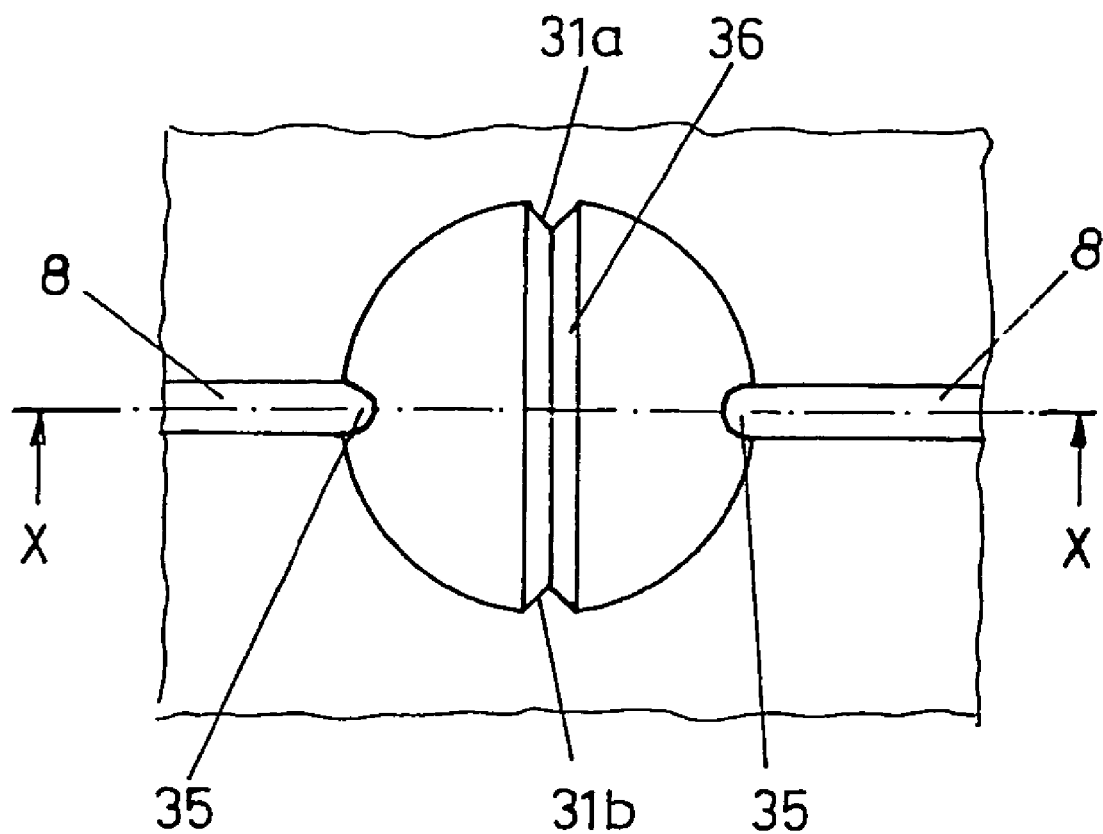
FIG. 9 shows an overhead view of a third valve in an actual version.
Figure 10:
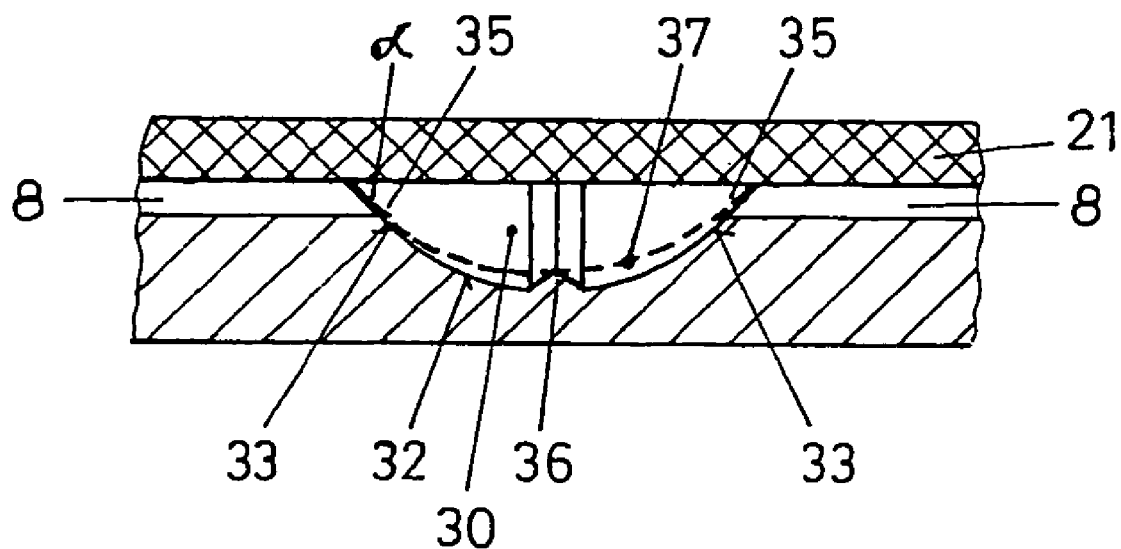
FIG. 10 shows a section through the valve according to FIG. 9 along the line X—X.

The valve which is shown in FIGS. 9 and 10 corresponds largely to the valve as shown in FIGS. 5 and 6. The recess 30 is spherically arched in contrast to the valve as shown in FIGS. 5 and 6. The recess 30 therefore seems circular in an overhead view. The recess 30 is divided by a link 36 into two halves which face the two entry openings 35 of the sections of the main channel 8. The link 36 extends from the first edge 31a to the opposing edge 31b of the recess. When the valve is closed the first film with its bottom as a result of the pressure acting on the first film 21 comes to rest at the top edge of the link 36. In this way, between the first film 21 and the bottom 37 of the first film 21 and the link 36 a sealed closure forms. A fluidic connection between the two halves of the recess 30 which lie on either side of the link 36 is thus no longer possible. A liquid thus cannot pass through the valve.

REFERENCE NUMBER LIST 1 inlet
2 first recesses/transfer means
3 first capillary stops
4 second recesses/metering means
5 second capillary stops
6 outlets
7 waste collector
8 main channel
9 secondary channel sections 10 secondary channel sections
11 secondary channel sections
12 secondary channel sections
13 channel to the waste collector
14 valves
20a first body
20b first body
21 membrane/prevention means
22 second body
23 (first) chamber
30 third recess
31, 31a, 31b edges of the third recess
32 bottom
33 lateral boundary surfaces
34 second chamber
35 entry openings
36 link
37 bottom of the film with the valve actuated
☐angle

The invention claimed is:

1. A device for parallel metering of a liquid comprising:
a first body
the first body has a main channel, secondary channels, one inlet, and outlets;
the main channel is connected to the inlet;
the secondary channels are connected to one outlet at a time;
the secondary channels are connected to the main channel;
at least one first chamber with a first pressure medium;
the first body has means for transferring pressure surges of the first pressure medium from a first chamber to the secondary channels;
each transfer means is connected to the secondary channels;
at least one means for preventing a fluidic connection between the secondary channels and the chamber is assigned to the transfer means.

2. The device as claimed in claim 1, wherein the device in the main channel has controllable means for fluidic decoupling.

3. The device as claimed in claim 2, wherein there are decoupling means between the inlet and the first connection of the main channel to one of the secondary channels and/or between all connections of the main channel and one of the secondary channels.

4. The device as claimed in claim 2, wherein the decoupling means are valves.

5. The device as claimed in claim 4, wherein the valves are formed by one third recess at a time and a first film or a second film or a third film.

6. The device as claimed in claim 5, wherein the second body and the first body encompass a second chamber which overlaps the first, second or third film in the area of the third recesses.

7. The device as claimed in claim 6, wherein the second chamber contains a second pressure medium.

8. The device as claimed in claim 6, wherein the first chamber and the second chamber can be separately triggered.

9. The device as claimed in claim 5, wherein the third recesses have lateral boundary surfaces which fall away flatly from at least one part of the edges to the bottom.

10. The device as claimed in claim 9, wherein the flatly sloping lateral boundary surfaces are tilted at an angle (α) between 5° and 45°.

11. The device as claimed in claim 9, wherein between the two inlet openings of the sections of the main channel into at least one part of the third recesses a bridge extends from the first edge via the lateral boundary surfaces and the bottom to the second edge.

12. The device as claimed in claim 5, wherein the third recesses have a concave arch.

13. The device as claimed in claim 12, wherein the arch is spherical.

14. The device as claimed in claim 12, wherein the arch is aspherical.

15. The device as claimed in claim 12, wherein the arch is cylindrical.

16. The device as claimed in claim 1, wherein the prevention means are sections of a first elastic and at least essentially impermeable film.

17. The device as claimed in claim 16, wherein the film is an elastomer.

18. The device as claimed in claim 16, wherein the first film lies on the first outside surface.

19. The device as claimed in claim 16, wherein the first film is attached to the first body by bonding.

20. The device as claimed in claim 1, wherein the main channel and the secondary channels are provided as grooves in the first outer surface of the first body.

21. The device as claimed in claim 1, wherein the main channel and/or the secondary channels are capillaries at least in sections.

22. The device as claimed in claim 21, wherein the sections of the secondary channels which adjoin the main channel are capillaries.

23. The device as claimed in claim 1, wherein the means for transferring pressure surges are made as first recesses.

24. The device as claimed in claim 23, wherein the first recesses are located on the first end of each secondary channel and the outlets are located on the second ends of each secondary channel.

25. The device as claimed in claim 23, wherein a first film covers at least the first recesses.

26. The device as claimed in claim 23, wherein a first film is attached to the body in the area of the first recess by bonding.

27. The device as claimed in claim 1, wherein the device further comprises a second body.

28. The device as claimed in claim 27, wherein the second body rests on the first film, the second body and a first film encompassing at least a first chamber.

29. The device as claimed in claim 28, wherein the first chamber with interposition of the first film is connected to the means for transferring pressure surges.

30. The device as claimed in claim 28, wherein the first chamber overlaps the first, second or third film in the area of a third recess.

31. The device as claimed in claim 27, wherein the second body has microstructure elements.

32. The device as claimed in claim 31, wherein the microstructure elements project into a first and/or a second chamber.

33. The device as claimed in claim 32, wherein the microstructure elements fix the first film on the first body.

34. The device as claimed in claim 32, wherein the first and/or second chamber has a height from 0.1 mm to 3 mm.

35. The device as claimed in claim 27, wherein the first and/or second chamber has a wall which is formed by one part of the second body and which can be deflected under the action of a means for producing a pressure surge into the interior of the chamber.

36. The device as claimed in claim 1, wherein the first pressure medium is under a pressure which has a first amount and which ensures that a first film is fixed on the first body.

37. The device as claimed in claim 1, wherein in the secondary channel sections there are means for metering the liquid.

38. The device as claimed in claim 37, wherein the metering means are provided between the outlets and the connection of the assigned secondary channel and the main channel.

39. The device as claimed in claim 38, wherein the metering means are second recesses in the first outside surface of the first body.

40. The device as claimed in claim 39, wherein the second recesses are covered by a first film.

41. The device as claimed in claim 34, wherein the first and/or the second chamber can be connected to a means for producing pressure surges.

42. The device as claimed in claim 41, wherein the means for producing the pressure surge is a piezoelectric element.

43. The device as claimed in claim 39, wherein the second recesses are covered by a second film.

44. The device as claimed in claim 41, wherein the device has a means for producing pressure surges.

* * * * *